United States Patent
Stokes et al.

(10) Patent No.: US 11,225,746 B2
(45) Date of Patent: Jan. 18, 2022

(54) SYSTEM AND TECHNIQUE FOR EXTRACTING PARTICULATE-CONTAINING LIQUID SAMPLES WITHOUT FILTRATION

(71) Applicant: Ecolab USA Inc., Saint Paul, MN (US)

(72) Inventors: Jimmy Maxwell Stokes, Cannon Falls, MN (US); Jason Gregory Lang, Bloomington, MN (US); Timothy Charles Nygaard, Hammond, WI (US)

(73) Assignee: Ecolab USA Inc., Saint Paul, MN (US)

( * ) Notice: Subject to any disclaimer, the term of this patent is extended or adjusted under 35 U.S.C. 154(b) by 159 days.

(21) Appl. No.: 16/552,767

(22) Filed: Aug. 27, 2019

(65) Prior Publication Data

US 2020/0063321 A1    Feb. 27, 2020

Related U.S. Application Data

(60) Provisional application No. 62/723,438, filed on Aug. 27, 2018.

(51) Int. Cl.
| | |
|---|---|
| *D06F 34/18* | (2020.01) |
| *G01N 1/14* | (2006.01) |
| *D06F 39/02* | (2006.01) |
| *G01N 33/18* | (2006.01) |
| *D06F 34/22* | (2020.01) |

(52) U.S. Cl.
CPC .............. *D06F 34/18* (2020.02); *D06F 34/22* (2020.02); *D06F 39/02* (2013.01); *G01N 1/14* (2013.01); *G01N 33/18* (2013.01)

(58) Field of Classification Search
CPC ...................................................... D06F 34/18
See application file for complete search history.

(56) References Cited

U.S. PATENT DOCUMENTS

| | | |
|---|---|---|
| 4,076,146 A | 2/1978 | Lausberg et al. |
| 4,509,543 A | 4/1985 | Livingston et al. |

(Continued)

FOREIGN PATENT DOCUMENTS

| | | |
|---|---|---|
| CA | 2409070 A1 | 4/2004 |
| CN | 101250802 A | 8/2008 |

(Continued)

OTHER PUBLICATIONS

International Patent Application No. PCT/US2019/048365, International Search Report and Written Opinion dated Dec. 9, 2019, 13 pages.

(Continued)

*Primary Examiner* — Jason Y Ko
(74) *Attorney, Agent, or Firm* — Fredrikson & Byron, P.A.

(57) ABSTRACT

A filtration-free liquid sampling system may be used to extract particulate or debris-containing liquid samples that may otherwise plug a filter over its service life. For example, such a system may be used to extract liquid sample from an industrial textile washer to monitor and/or validate the quality of wash conditions within the washer. In some examples, the system includes a pump that creates a vacuum on a backstroke, drawing liquid into a sensor housing positioned between the pump and the washer. After holding the liquid in the sensor housing long enough to measure its properties, the pump can be driven in a reverse stroke to pressurize the contents in the sensor housing and force the liquid back into the washer. This vacuum fill/pressure purge can keep the sensor housing free of debris.

25 Claims, 4 Drawing Sheets

(56) References Cited

U.S. PATENT DOCUMENTS

| | | |
|---|---|---|
| 5,536,663 A | 7/1996 | Mueller-Kirschbaum et al. |
| 6,237,807 B1 | 5/2001 | Uhl et al. |
| 6,377,868 B1 | 4/2002 | Gardner |
| 6,456,375 B1 | 9/2002 | Ottens et al. |
| 6,536,060 B1 | 3/2003 | Janssens et al. |
| 6,892,143 B2 | 5/2005 | Howes, Jr. et al. |
| 6,918,398 B2 | 7/2005 | Edelmann et al. |
| 7,950,256 B2 | 5/2011 | Grimm et al. |
| 8,187,540 B2 | 5/2012 | Mehus et al. |
| 9,567,702 B2 | 2/2017 | Seo et al. |
| 2002/0088502 A1 | 7/2002 | Van Rompuy et al. |
| 2003/0106164 A1 | 6/2003 | Metzger-Groom et al. |
| 2004/0122555 A1 | 6/2004 | Howes, Jr. et al. |
| 2004/0236522 A1 | 11/2004 | Howes, Jr. et al. |
| 2004/0265174 A1 | 12/2004 | Mehus et al. |
| 2005/0096788 A1 | 5/2005 | Peterson et al. |
| 2005/0149273 A1 | 7/2005 | Peterson et al. |
| 2006/0007444 A1 | 1/2006 | Oon et al. |
| 2007/0144274 A1 | 6/2007 | Gibson et al. |
| 2008/0017221 A1 | 1/2008 | Fife et al. |
| 2008/0176250 A1 | 7/2008 | Banks |
| 2008/0176260 A1 | 7/2008 | Banks |
| 2009/0231581 A1 | 9/2009 | Han et al. |
| 2010/0116689 A1 | 5/2010 | Greene et al. |
| 2010/0141460 A1 | 6/2010 | Tokhtuev et al. |
| 2010/0281625 A1 | 11/2010 | Oh et al. |
| 2011/0253606 A1 | 10/2011 | Chan et al. |
| 2011/0320133 A1 | 12/2011 | Mehus et al. |
| 2012/0231549 A1 | 9/2012 | Miller |
| 2012/0324995 A1 | 12/2012 | Tincher et al. |
| 2013/0042652 A1 | 2/2013 | Brueckner et al. |
| 2013/0278921 A1 | 10/2013 | Choi et al. |
| 2016/0010269 A1 | 1/2016 | Testa et al. |
| 2016/0120391 A1 | 5/2016 | Freudenberg et al. |
| 2017/0050870 A1 | 2/2017 | Brezoczky et al. |

FOREIGN PATENT DOCUMENTS

| | | |
|---|---|---|
| CN | 201258402 Y | 6/2009 |
| CN | 102199852 A | 9/2011 |
| CN | 102720034 A | 10/2012 |
| CN | 203096432 U | 7/2013 |
| CN | 203923708 U | 11/2014 |
| CN | 106048986 A | 10/2016 |
| CN | 106758013 A | 5/2017 |
| DE | 2543352 A1 | 4/1977 |
| DE | 3526563 A1 | 2/1987 |
| DE | 3640114 A1 | 6/1988 |
| DE | 4204806 A1 | 8/1993 |
| DE | 4228021 A1 | 3/1994 |
| DE | 4311064 A1 | 10/1994 |
| DE | 4342272 A1 | 6/1995 |
| DE | 4412576 A1 | 10/1995 |
| DE | 19533927 A1 | 3/1997 |
| DE | 19534431 A1 | 3/1997 |
| DE | 19721976 A1 | 12/1998 |
| DE | 19814500 A1 | 10/1999 |
| DE | 19852164 A1 | 5/2000 |
| DE | 10237853 A1 | 3/2004 |
| DE | 102006029950 A1 | 1/2008 |
| DE | 102009032964 A1 | 3/2011 |
| DE | 102010002589 A1 | 9/2011 |
| DE | 102011015188 A1 | 9/2011 |
| DE | 102012205827 A1 | 10/2013 |
| DE | 102012208663 A1 | 11/2013 |
| DE | 102012105961 A1 | 1/2014 |
| DE | 102012018539 A1 | 3/2014 |
| EP | 509328 A2 | 10/1992 |
| EP | 473625 B1 | 8/1993 |
| EP | 992622 A2 | 4/2000 |
| EP | 1063340 A1 | 12/2000 |
| EP | 1092384 A2 | 4/2001 |
| EP | 1321566 A1 | 6/2003 |
| EP | 1500738 A1 | 1/2005 |
| EP | 1707663 A1 | 10/2006 |
| EP | 1978141 A2 | 10/2008 |
| EP | 2014816 A1 | 1/2009 |
| EP | 2053151 A2 | 4/2009 |
| EP | 2261414 A1 | 12/2010 |
| EP | 2290148 A1 | 3/2011 |
| EP | 2319382 A1 | 5/2011 |
| EP | 2434039 A1 | 3/2012 |
| EP | 2434043 A1 | 3/2012 |
| EP | 2644079 A1 | 10/2013 |
| EP | 2767825 A1 | 8/2014 |
| EP | 2789723 A1 | 10/2014 |
| ES | 2412960 A1 | 7/2013 |
| FR | 2594149 A1 | 8/1987 |
| GB | 1401426 A | 7/1975 |
| GB | 1508469 A | 4/1978 |
| GB | 2078946 A | 1/1982 |
| GB | 2217050 A | 10/1989 |
| IT | 1170345 B | 6/1987 |
| JP | S61056000 B2 | 5/1979 |
| JP | S60072599 A | 4/1985 |
| JP | S63229092 A | 9/1988 |
| JP | H0835945 A | 2/1996 |
| JP | H08276100 A | 10/1996 |
| JP | H09210776 A | 8/1997 |
| JP | H10170498 A | 6/1998 |
| JP | 2000051577 A | 2/2000 |
| JP | 2002360973 A | 12/2002 |
| JP | 2004317454 A | 11/2004 |
| JP | 2007198915 A | 8/2007 |
| JP | 2009095275 A | 5/2009 |
| JP | 2011045433 A | 3/2011 |
| WO | 9209017 A1 | 5/1992 |
| WO | 9958990 A2 | 11/1999 |
| WO | 02068940 A1 | 9/2002 |
| WO | 02068941 A1 | 9/2002 |
| WO | 03100153 A1 | 12/2003 |
| WO | 2004007828 A1 | 1/2004 |
| WO | 2004053220 A1 | 6/2004 |
| WO | 2007143047 A1 | 12/2007 |
| WO | 2008065613 A1 | 6/2008 |
| WO | 2009033016 A2 | 3/2009 |
| WO | 2011085808 A1 | 7/2011 |
| WO | 2011161069 A2 | 12/2011 |
| WO | 2012026821 A1 | 3/2012 |
| WO | 2014207125 A1 | 12/2014 |
| WO | 2016127211 A1 | 8/2016 |
| WO | 2016146313 A1 | 9/2016 |

OTHER PUBLICATIONS

Micro Diaphragm Liquid Pumps NF 30, KNF Neuberger, Inc., Section 200.20, Nov. 2011, 6 pages.

Water Conservation for On-Premis Laundries, Pellerin Milnor Corp., 2014, 2 pages.

Operating Instructions Testomat ECO, Lenntech, date unknown, 49 pages.

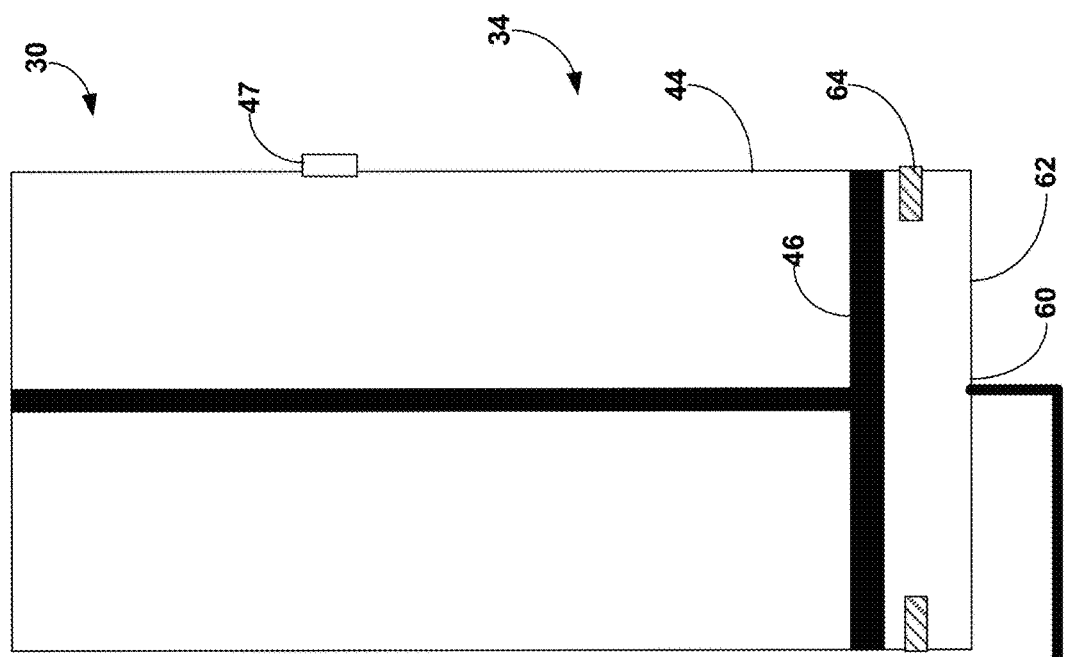
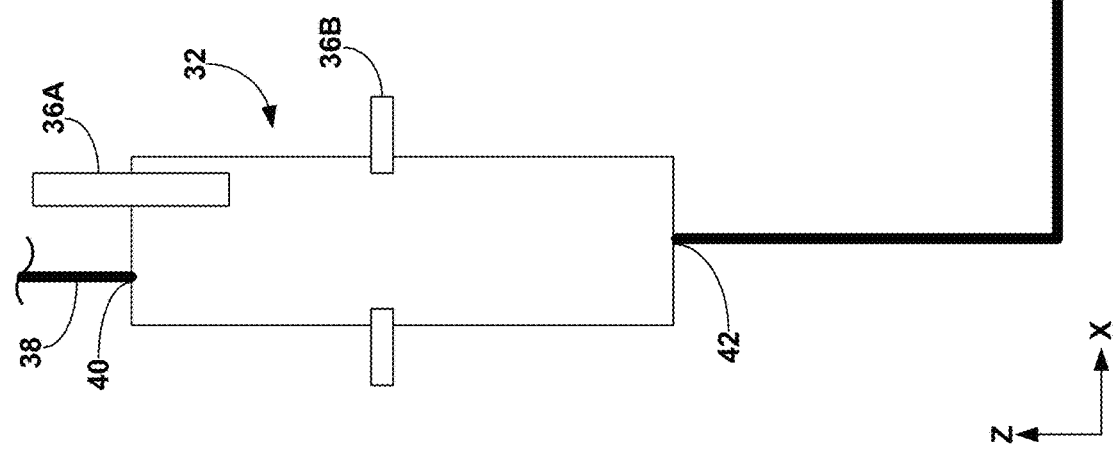
FIG. 3

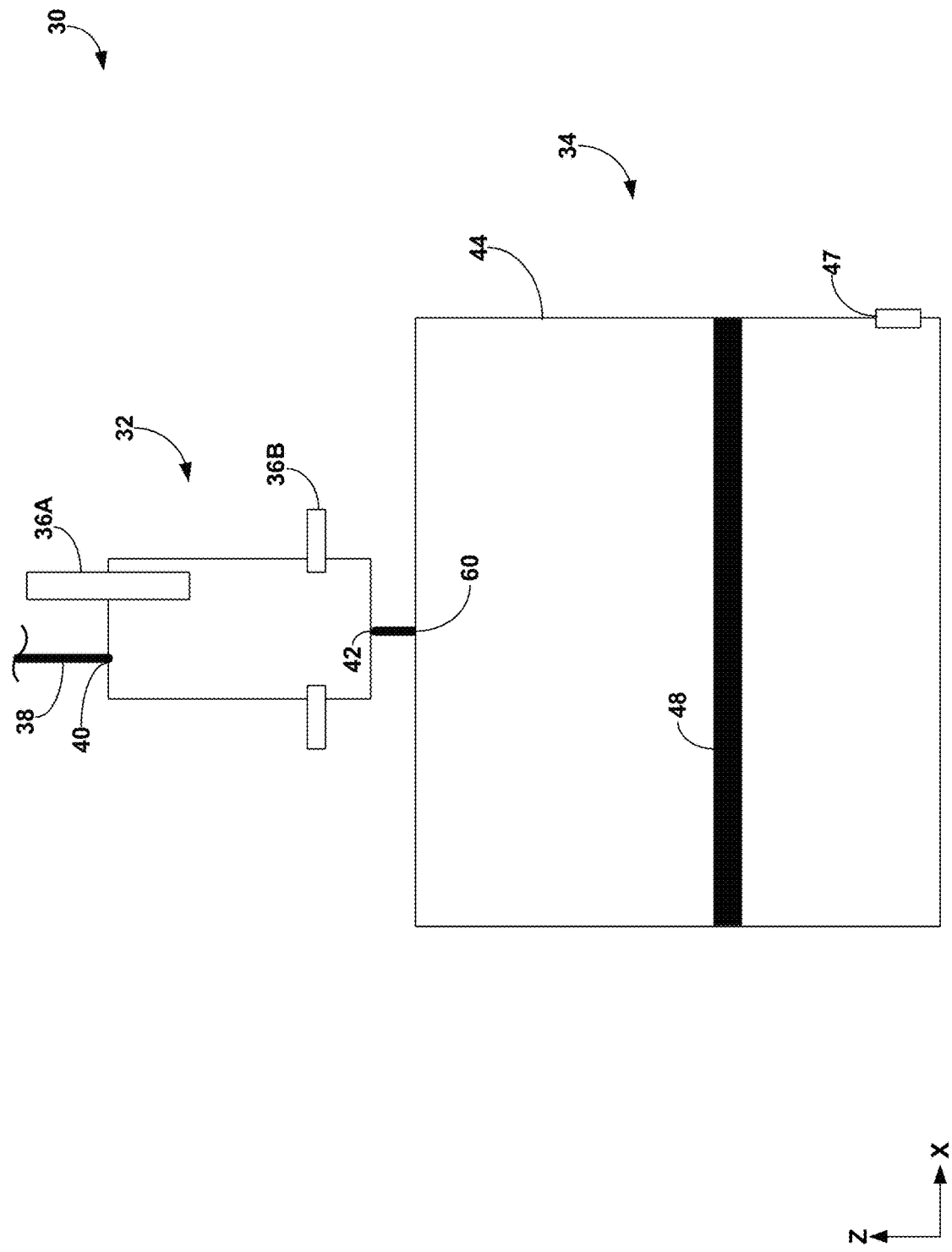

SYSTEM AND TECHNIQUE FOR EXTRACTING PARTICULATE-CONTAINING LIQUID SAMPLES WITHOUT FILTRATION

CROSS-REFERENCE

This application claims the benefit of U.S. Provisional Patent Application No. 62/723,438, filed Aug. 27, 2018, the entire contents of which are incorporated herein by reference.

TECHNICAL FIELD

This disclosure relates to liquid samplers for extracting particulate-containing liquid samples for analysis and, more particularly, to liquid samplers used to extract and analyze liquid samples from commercial textile washers.

BACKGROUND

Operators in the commercial textile cleaning industry are continually challenged to process high volumes of textile articles that are often heavily soiled to produce hygienic and visually attractive items for reuse. Typical textiles that are processed in high volume commercial cleaning facilities include hospital articles (e.g., bed linens, surgical and patient garments, towels), hotel and hospitality articles (e.g., bed linens and toweling), and restaurant articles (e.g., table cloths, napkins).

Commercial textile cleaners typically use large, automated commercial washing machines to clean the textiles. These commercial washing machines may automatically add a series of different aqueous solutions to the textiles being processed, such as aqueous solutions containing quantities of alkaloid, detergent, bleach, starch, softener and/or sour, to clean and sanitize/disinfect the articles being processed. The concentration of the different chemical agents introduced into the washing machine during processing may be preprogrammed based on the expected level of soil on the textiles being processed and the characteristics of the textiles being processed (e.g., color, desire softness).

In practice, the type and extent of soil on a particular textile being washed can vary widely depending on the environment and conditions the textile was exposed to before being deposited for cleaning. For example, hospital linens received for washing may be no dirtier than those from a typical hotel room used in normal service. Alternatively, that set of hospital linens may be heavily contaminated with infectious biological fluids from a patient. The amount of washing time and/or concentration of chemical additives needed to properly clean and sanitize/disinfect the heavily contaminated linens can be significantly greater than the linens subject to normal use. If the amount of chemical additive preprogrammed to be introduced into the washer is too great to cover the most soiled articles possible, most wash cycles will overdose on chemical additive, resulting in excessive cleaning cost and wear on the articles being cleaned. By contrast, if the amount of chemical additive preprogrammed to be introduced into the washer is too little for the solid demands of the article being washed, the article may not be properly cleaned and sanitized/disinfected.

SUMMARY

In general, this disclosure is directed to systems and techniques for extracting liquid samples for analysis from a larger source of the liquid. The liquid may be a particulate-containing liquid that carries solid matter entrained in the liquid. For example, in the case of aqueous liquid extracted from a washing machine, the liquid may contain dirt, sand, lint and/or other sheared textile material, and/or released remnants of soil deposited on the surface of the articles being cleaned. In practice, these solid materials carried in the liquid being sampled may have a tendency to plug or otherwise foul a sample extraction device. If a screen is placed between the source of liquid being sampled and the sample extraction device, the pores of the screen may plug with the solid material over time, rendering the sample extraction device in operable unless an operator intervenes to clean the screen.

In accordance with some examples of the present disclosure, a sample extraction device may be configured to extract samples of liquid material from the larger source for analysis without passing the sample liquid through a screen that can be plugged. The sample extraction device may have a sensor housing and a liquid conveyance device. The sensor housing can contain one or more sensors for analyzing liquid extracted from the larger source. The sensor housing may be positioned between the larger source of liquid being sampled and the liquid conveyance device. The liquid conveyance device may generate a vacuum pressure to draw liquid from the larger source to the liquid conveyance device, causing the liquid sample to be drawn into the sensor housing positioned between the larger liquid source and the conveyance device. The liquid conveyance device may also generate a positive pressure to expel the liquid drawn toward the conveyance device back away from the conveyance device. For example, after drawing liquid into the sensor housing and holding the liquid for a period of time sufficient for the liquid to be analyzed, the liquid conveyance device may generate a positive pressure expelling the liquid from the sensor housing. This positive pressure may also expel any solid material drawn into the sensor housing with the liquid being analyzed, effectively purging the sensor housing of falling and/or plugging solid material.

While a liquid conveyance device used as part of a sampling system can have a variety of different configurations, in some examples, the liquid conveyance device includes a motive element that moves in one direction to create a vacuum drawing liquid into the sensor housing and moves in the reverse direction to discharge liquid out of the sensor housing. For example, the motive element may be implemented using a piston or a flexible membrane. The motive element may be configured to draw a volume of liquid into the liquid conveyance device greater than the volume of the sensor housing. This can help ensure that enough liquid is drawn from the liquid source to fill the sensor housing and/or that the entire volume of the sensor housing is substantially entirely flushed when expelling the sampled liquid out of the housing.

In some configurations, the sampling system may have a single fluid opening through which liquid being sampled is both drawn into the sampling system and expelled from the sampling system. That is, rather than having an inlet opening through which liquid is drawn into the system and a separate outlet opening through which the liquid is subsequently discharged, the system may be implemented with a single fluid opening that functions as both an inlet and an outlet depending on the direction of liquid flow. This arrangement can be useful to provide bidirectional flow through the sampling system, including the sensor housing of the sampling system. When so configured, liquid may be drawn from the liquid source (e.g., textile washer) through the single opening into the sensor housing for analysis. After being analyzed, the liquid may be expelled the back out of the sensor housing through the same opening, optionally returning to the liquid source from which it was drawn. This bidirectional flow pattern can provide agitation to release and remove solid material drawn into the sensor housing with the liquid being sampled, helping to purge the sensor housing of potentially fouling material.

In one example, a liquid sampling system for an industrial textile washer is described. The system includes a tunnel washer having an inlet, an outlet, and a plurality of processing chambers between the inlet and the outlet. The system also includes a liquid sampling system having a fluid line in fluid communication with at least one of the plurality of processing chambers of the tunnel washer. The example specifies that the liquid sampling system includes a sensor housing, at least one sensor, and a liquid conveyance device. The sensor housing has a first opening connected to the fluid line and a second opening. The sensor is positioned to measure a property of a liquid drawn into the sensor housing. The liquid conveyance device having an opening in fluid communication with the second opening of the sensor housing and a motive element. In the example, the motive element is configured to draw a volume of liquid into the liquid conveyance device through the opening, thereby drawing liquid from the at least one of the plurality of processing chambers of the tunnel washer via the fluid line and into the sensor housing. The motive element is further configured to subsequently discharge the volume of liquid from the liquid conveyance device back out through the opening, thereby pushing the liquid in the sensor housing out of the sensor housing.

In another example, a method is described that includes drawing a sample of liquid out of a processing chamber of a textile washer by driving a motive element of a liquid conveyance device in fluid communication with the processing chamber. The example specifies that there is a sensor housing positioned between the motive element and the processing chamber. Accordingly, driving the motive element of the liquid conveyance device fills the sensor housing with liquid from the processing chamber. The method includes measuring a property of the liquid drawn into the sensor housing using a sensor. The method further involves pushing the liquid drawn into the sensor housing back out of the sensor housing and back into the processing chamber of the textile washer by driving the motive element of the liquid conveyance device.

In another example, a liquid sampling system is described that includes a sensor housing, at least one sensor, and a liquid conveyance device. The sensor housing has a first opening and a second opening and that defines a volume within the sensor housing. The sensor is positioned to measure a property of a liquid drawn into the sensor housing. The liquid conveyance device has an opening in fluid communication with the second opening of the sensor housing and a motive element. The motive element is configured to draw a volume of the liquid greater than the volume of the sensor housing into the liquid conveyance device via the opening, thereby drawing liquid into the sensor housing. The motive element is further configured to subsequently discharge the volume of liquid drawn into the liquid conveyance device back out through the opening.

The details of one or more examples are set forth in the accompanying drawings and the description below. Other features, objects, and advantages will be apparent from the description and drawings, and from the claims.

BRIEF DESCRIPTION OF DRAWINGS

FIG. 3 is a sectional side view of another example configuration of a liquid sampling system.

FIG. 4 is a sectional side view of another example configuration of a liquid sampling system.

DETAILED DESCRIPTION

The present disclosure is generally directed to systems, devices, and techniques for extracting and analyzing liquid fluid from a piece of equipment containing the fluid. The equipment itself may not allow direct analysis of fluid inside of the equipment, necessitating that fluid be taken out of the equipment for analysis. For example, the operating conditions inside of the equipment may be too harsh to accommodate positioning a sensor inside of the equipment for direct measurement of the fluid in the equipment. Additionally or alternatively, the equipment may have been designed without the features needed for direct sensory measurement of liquid inside of the equipment. As a result, an external liquid sampling system may be useful to retrofit the equipment with sensory capabilities.

In accordance with some examples described in this disclosure, a liquid sampling system is provided for extracting and analyzing liquid from one or more pieces of equipment housing the bulk of the liquid. The liquid sampling system can be used with any type of equipment that process liquid media, including those types of equipment where the liquid being processed contains intermixed solid matter that has a tendency to plug or foul filtration media. Example equipment with which the liquid sampling system may be used includes, but is not limited to, cooling water systems (e.g., cooling water towers), heat exchangers, petrochemical processing and extraction equipment, mining drainage and waste water systems, warewash machines, pool and spa systems, poultry chillers, produce flumes, food processing plants, pulp and paper streams and wastewater operations.

As one example, the sampling system may be used to extract samples of liquid from a textile washer to evaluate the characteristics of liquid and, correspondingly, to help determine and/or validate the chemical conditions under which the textiles being processed are cleaned. Liquid within a textile washer has been found, in some applications, to contain high levels of solid material that has a tendency to cause fouling and/or plugging problems. This solid material can include dirt, sand, lint and/or other sheared textile material, and/or released remnants of soil deposited on the surface of the articles being cleaned. The solid material that is dispersed throughout the liquid in these applications has a tendency to agglomerate and bind together, forming plugging challenges for a sampling apparatus over multiple sample extractions an extended service. Accordingly, example sampling system configurations are described below with reference to an example textile washing system in which the sampling system may be implemented. It should be appreciated, however, that the disclosure is not limited in this respect unless otherwise noted, and a sampling system can be used in other applications.

Figure 1:
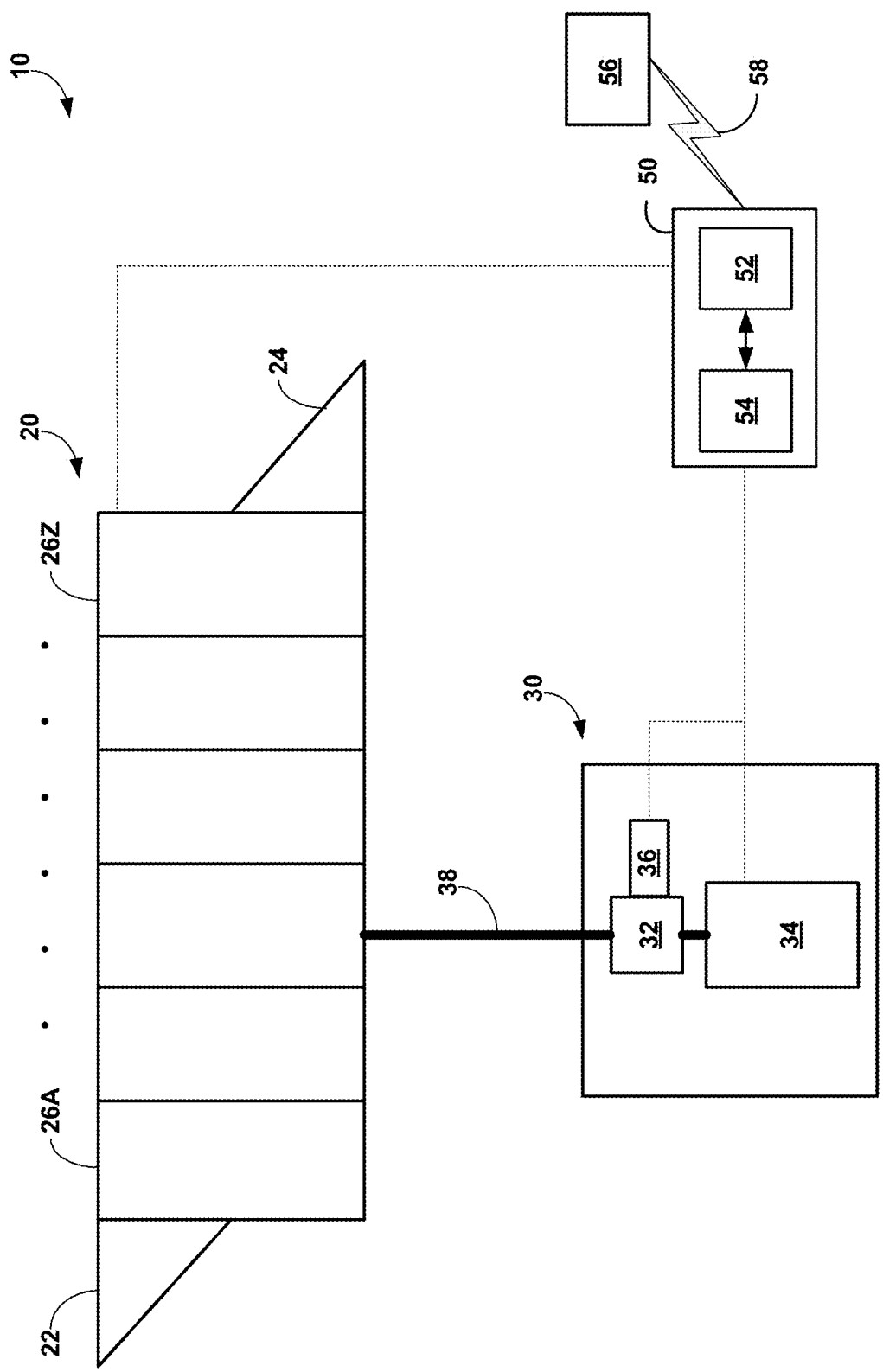
FIG. 1 is an illustration of an example textile washing system that may utilize a liquid sampling system according to disclosure.

FIG. 1 is an illustration of an example textile washing system 10 that may utilize a liquid sampling system according to disclosure. System 10 includes a tunnel washer 20 and a liquid sampling system 30 that is in fluid communication with the tunnel washer 20. Tunnel washer 20 has an inlet 22 that receives articles to be washed and an outlet 24 that discharges washed articles. As described in greater detail below, liquid sampling system 30 can extract a sample of liquid from an interior of tunnel washer 20 to analyze one or more characteristics of the liquid. The characteristic(s) of the liquid analyzed may indicate the chemical and/or biological conditions of the liquid within the washer. These characteristic(s) may be compared to one or more stored thresholds to validate that the appropriate amount of chemistry was added and present in the washer to achieve cleaning and/or sanitization/disinfection conditions needed for the articles being washed. If the conditions are not met, additional chemistry may be introduced into the washer while the articles are still being processed in the washer or the articles may be rewashed under appropriate treatment conditions.

Tunnel washer 20 may be implemented as a continuous batch tunnel washer that includes a screw or conveying member to continuously transport articles being washed from inlet 22 to outlet 24, e.g., while periodically holding the articles within a section of the wash chamber for agitation before moving onto the next section. Wash liquid within the tunnel washer 20 may move in a co-current or counter-current direction through the washer. While FIG. 1 illustrates textile washing system 10 as having a tunnel washer, in other applications, the washing system may utilize a centrifuge washing machines provided with a rotatable washing drum or yet other type of apparatus that provides mechanical agitation between washing liquid and the articles being washed. For example, a textile washer used in washing system 10 may side-load textile washer with one or more processing chambers, an end loader washer/extractor, an open pocket washer/extractor, or yet other type of textile washing device.

When textile washing system 10 includes tunnel washer 20, the interior of the tunnel washer may be divided into multiple zones, sections, pockets, or compartments, e.g., that provide processing chambers functioning as different stages of the washing process. For example, tunnel washer 20 may include multiple processing chambers 26A-26Z (collectively referred to as "processing chamber 26") through which the textile articles being processed progresses during various wash and rinse cycles. Tunnel washer 20 is illustrated as having six processing chambers 26 but may have fewer processing chambers (e.g., three, four, five) or more processing chambers (e.g., 8, 10, 12, or more).

To define the different processing stages 26 of tunnel washer 20, an Archimedean screw may extend along the length of the tunnel washer with the helixes of the screw dividing the interior into different processing chamber. Tunnel washer 20 can be mounted on rollers, allowing the tunnel washer to oscillate back and forth to agitate laundry articles within a given processing chamber 26 for a period of time. Tunnel washer 20 may rotate 360 degrees periodically, causing the articles being processed to move from one processing chamber 26 to the next processing chamber. Alternatively, the screw may turn 360 degrees forward instead of the tunnel washer housing to move the articles being processed from one stage to the next.

In general, tunnel washer may include one or more wash chamber(s), one or more oxidizing chamber(s), and one or more rinse chamber(s) moving sequentially from inlet 22 to outlet 24. Within the one or more wash chambers, the articles being washed may be wetted and washed in the initial break step with detergents, surfactants, chelants, water conditioners, and/or alkalis, in each case with heating or unheated. After being washed, the articles may be conveyed downstream to the oxidizing chamber(s). Within the oxidizing chamber(s), antimicrobial agents, bleaches, chelants, water conditioners, pH adjustment acids/bases, and/or quaternary ammonium compounds may be added to clean and sanitize/disinfect the articles. The articles being washed can then be conveyed further down the tunnel washer to the rinse (and/or sour and/or finishing) chamber(s). Within the rinse/sour/finishing chamber(s), the articles may be rinsed with clean water, pH adjusted by adding antichlors and/or sour materials containing acid components that neutralize alkaline residues on the fabric, treated with a fabric softening agent, and/or treated with a bacteriostatic, mildewcide, and/or antistatic agent. In some examples, a separate neutralization processing chamber is provided downstream of the rinse processing chamber(s) for adjusting the pH of the articles before discharge. At the outlet 24 of tunnel washer 20, a water extractor or press may remove excess water from the articles being washed, allowing the damp articles to be sent further downstream for drying, ironing, and/or steam finishing.

Any types of fabric articles can be washed in textile washing system 10. Example articles include clothing, linens, towels, blankets, and the like. The articles may be manufactured from natural fibers (e.g., wool, cashmere, cotton, silk, linen, hemp) and/or synthetic fibers (e.g., rayon, polyester, acrylic, acetate and nylon). Depending on the use environment of the articles, the articles may carry a variety of different types of soils. Example soils include dirt (e.g., sand), food and/or beverage deposits, bodily fluid (e.g., blood, fecal material), and/or other contaminants. Accordingly, liquid samples extracted from tunnel washer 20 may have greater than 0.1 weight percent solids, such as greater than 0.25 weight percent solids, or greater than 0.5 weight percent solids. For example, the liquid samples may have from 0.05 to 5 weight percent solids, such as from 0.1 to 3 weight percent solids, or from 0.25 to 2 weight percent solids. The solids may have an average size greater than 25 microns, such as an average size greater than 50 microns, an average size greater than 100 microns, or an average size greater than 250 microns. For example, at least 90% of the solids may fall within a size distribution ranging from 50 microns to 1 mm. For applications involving larger solids, at least 90% of the solids may fall within a size distribution ranging from 0.1 mm microns to 5 mm. Other size ranges of solid materials in the liquid being sampled may be present depending on the application and nature of the fluid being sampled.

To evaluate one or more characteristics of liquid within tunnel washer 20, textile washing system 10 includes liquid sampling system 30. As will be described in greater detail below with respect to FIGS. 2-4, liquid sampling system 30 may include a sensor housing 32 and a liquid conveyance device 34. Sensor housing 32 can define a cavity that receives liquid from tunnel washer 20 and allows one or more sensors 36 to interact with liquid in the cavity to determine one or more characteristics of the liquid. Liquid conveyance device 34 can draw liquid into sensor housing 32 for analysis and discharge liquid from the sensor housing after analysis is complete.

Textile washing system in the example of FIG. 1 also includes a controller 50. Controller 50 is communicatively connected to liquid sample system 30 and, may also optionally be communicatively connected to tunnel washer 20, as shown in the illustrated example. Controller 50 includes processor 52 and memory 54. Controller 50 can communicate with controllable components in system 10 via wired and/or wireless connections. For example, controller 50 can communicate with liquid sampling system 30, e.g., to receive signals generated by one or more sensors 36 analyzing liquid in sensor housing 32 and/or to control liquid conveyance device 34 to fill and discharge the sensor housing of liquid. In some configurations, controller 50 can also control tunnel washer 20, e.g., in response to information generated by liquid sampling system 30 concerning one or more characteristics of liquid within the tunnel washer. When so implemented, controller 50 may control operational characteristics of the tunnel washer (e.g., wash residence time within a processing chamber, amount of agitation, the introduction and/or discharge of water and/or cleaning chemicals, detergent, etc.) in response to information generated by liquid sampling system 30.

Processor 52 runs software stored in memory 54 to perform functions attributed to textile washing system 10 in this disclosure, including liquid sampling system 30 and any sensors 36 associated therewith. Components described as processors within controller 50, or any other device described in this disclosure, may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 54 stores software and data used or generated by controller 52. For example, memory 54 may store data used by controller 52 to control liquid sampling system 30 to extract a liquid sample using liquid conveyance device 34, analyze the liquid sample using the one or more sensors 36 to determine one or more characteristics of the sample, and to further control liquid conveyance device 34 to discharge the analyzed sample. Memory 54 may store the determined characteristic(s) of the liquid, e.g., along with information associating the determined characteristic(s) to a particular batch textiles being washed and/or particular textile articles being washed in that batch. This information can be useful to validate the washing characteristics that a particular textile article was exposed to, e.g., giving downstream users of the article that the article was appropriately cleaned and/or sanitized/disinfected during the earlier washing process.

To sample liquid from tunnel washer 20 using liquid sampling device 30, the liquid sampling system may be placed in fluid communication with the tunnel washer. Liquid sampling system 30 may be placed in fluid communication by establishing a flow pathway from an interior of the device from which the liquid sample is being extracted (e.g., tunnel washer 20) to the liquid sampling system. In some configurations, sensor housing 32 of liquid sampling system 30 is connected directly to tunnel washer 20, for example to provide a housing-to-housing connection without intervening conduit. In other configurations, a fluid conduit is connected on one end to tunnel washer 20 and the opposite end to liquid sampling system 30 (e.g., sensor housing 32 of the liquid sampling system). The fluid conduit may be a pipe or segment of tubing that allows fluid to be conveyed from one location to another location in the system. The material used to fabricate the conduits should be chemically compatible with the liquid to be conveyed and, in various examples, may be steel, stainless steel, or a polymer (e.g., polypropylene, polyethylene, polyvinylidene difluoride). In either configuration, a fluid line 38 (e.g., provided by a section of housing and/or an intermediate fluid conduit) may be provided between tunnel washer 20 and liquid sampling system 30.

Depending on the configuration of tunnel washer 20, the washer may have an existing port or valve connection that can be used to fluidly couple liquid sampling system 30 the tunnel washer. If tunnel washer 20 does not have an existing opening that can be used to make a fluid connection, a user may install a port on the tunnel washer for making the connection. The port on tunnel washer 20 used to provide fluid communication with liquid sampling system 30 may be located sufficiently low on the tunnel washer housing to be below the liquid level inside the housing, e.g., on a bottom-most surface of the housing.

Liquid sampling system 30 may be fluidly coupled to one or more processing chambers 26 of tunnel washer 20. For example, tunnel washer 20 may have multiple ports each of which provide fluid communication with a different processing chamber 26 of the tunnel washer. One or more fluid lines 38 can provide fluid communication between the different processing chambers 26 and liquid sampling device 30. For example, a valve manifold may be used to control fluid communication between the multiple different processing chambers and liquid sampling system 30. Liquid sampling system 30 may extract liquid from a select one of the processing chambers 26 by controlling the valve positioning of the valve manifold.

In other examples, liquid sampling system 30 may be in fluid communication with only a single processing chamber. In these examples, the fluid characteristics of only the single processing chamber 26 of tunnel washer 20 in fluid communication with liquid sampling system 30 may be monitored. Alternatively, multiple liquid sampling systems 30 may be implemented in textile washing system 10. Each of the multiple liquid sampling systems 30 may have the design features of a liquid sampling system as described herein. Each of the multiple liquid sampling systems 30 may be fluidly connected to a different processing chamber 26. In this way, the fluid characteristics of liquids from different processing chambers 26 of tunnel washer 20 may be monitored. When textile washing system 10 is implemented using multiple liquid sampling systems 30, each liquid sampling system may have its own controller (e.g., which in turn communicates with a system controller) and/or a single controller may control all the liquid sampling systems. In either case, multiple liquid sampling systems 30 may be mounted on a shared mobile cart, allowing the multiple liquid sampling systems to be transported together as a system.

While liquid sampling system 30 can be used to extract liquid from any location for analysis, in some examples, the liquid sampling system is fluidly connected to a wash processing chamber 26 of tunnel washer 20. For example, when tunnel washer 20 includes multiple processing chambers 26 that include a wash processing chamber, an oxidizing processing chamber, and a rinse processing chamber (with additional processing chambers optionally present), liquid sampling system 30 may be fluidly connected to a wash processing chamber. In general, tunnel washer 20 may have one or more wash processing chambers 26 where chemistry is introduced to clean and/or sanitize/disinfect the textile articles being cleaned.

The amount of chemistry introduced into the one or more wash processing chambers 26 may be effective to ensure that the textile articles washed using tunnel washer 20 are cleaned and sanitized/disinfected through the wash process. The amount of chemistry to be introduced into the one or more wash processing chambers to achieve the desired level of cleaning and/or sanitization/disinfection may vary depending on the types and amounts of soil present on the articles being cleaned. The amount of chemistry consumed during the washing process may vary depending on the types and amount of soil present on the articles being cleaned. Accordingly, monitoring the characteristics of the liquid in one or more wash processing chambers 26 of tunnel washer 20 may be useful to determine if a threshold level of chemistry is present in the liquid in which the textiles are being washed.

In operation, controller 50 can control liquid sampling system 30 to extract a liquid sample from the processing chamber 26 to which the liquid sampling system is fluidly connected. For example, controller 50 can control liquid conveyance device 34 to draw liquid from processing chamber 26 via fluid line 38 into sensor housing 32. Controller 50 can further control one or more sensors 36 of liquid sampling system 30 to analyze one or more characteristics of the fluid drawn into sensor housing 32. Controller 50 can subsequently control liquid conveyance device 34 to discharge the liquid in sensor housing 32 having undergone analysis back out of the sensor housing. In some applications, liquid drawn from processing chamber 26 is discharged back into the same processing chamber after having undergone analysis. In other applications, the liquid having undergone analysis is discharged to a drain or other disposal location.

Although not illustrated in the example of FIG. 1, a valve may be interposed between tunnel washer 20 and liquid sampling system 30, e.g., along fluid line 38. Controller 50 may control the valve to open fluid line 38 for extracting a sample from processing chamber 26, close the valve while the fluid sample is undergoing analysis, and reopen the valve to discharge the analyzed fluid sample back through fluid line 38. In other configurations, system 10 may not have a valve interposed between tunnel washer 20 and liquid sampling system 30. Rather, fluid line 38 may be in direct fluid connection with tunnel washer 20 thought the extraction, sampling, and discharge processes. When so configured, liquid conveyance device 34 can cycle to draw liquid into the sampling system, hold the drawn liquid in the system during sampling (while maintaining fluid contact via fluid line 38), and cycle again to discharge the liquid back into the tunnel washer. The cycling may be controlled, for example, by controller 50 controlling an air source that pneumatically drives liquid conveyance device 34.

Controller 50 can control liquid sampling system 30 to extract and analyze liquid samples with any desired frequency. In one configuration, controller 50 controls liquid sampling system 30 to extract and analyze one liquid sample from processing chamber 26 during each batch of textiles processed in the washer. In another configuration, controller 50 controls liquid sampling system 30 to extract and analyze multiple liquid samples from processing chamber 26 during each batch of textiles being processed in the washer. For example, controller 50 may control liquid sampling system 30 to repeatedly extract, analyze, and discharge liquid from a given processing chamber 26 while textile articles being washed remain in that processing chamber undergoing washing. As examples, controller 50 may control liquid sampling system 30 to extract, analyze, and discharge a sample at least once every minute, such as at least once every 30 seconds, at least once every 10 seconds, or at least once every 5 seconds. Additionally or alternatively, controller 50 may include a user interface that allows an operator to interact with the controller to control liquid sampling system 30 on demand to extract and analyze liquid sample as desired.

Operating under the control of controller 50, the one or more sensors 36 of liquid sampling system 30 can analyze one or more characteristics of the liquid drawn into the liquid sampling system. Example types of sensors that may be used as sensors 36 on liquid sampling system 30 include a temperature sensor, a pH sensor, a conductivity sensor, an optical sensor, and combinations thereof. The sensor(s) 36 may be used to determine a concentration of one or more chemical components present in the liquid. In the example configuration of FIG. 1, for instance, sensor(s) 36 may determine a one or more characteristics relating to the cleaning and/or sanitizing/disinfection efficacy of the liquid undergoing analysis. Such characteristics may include the concentration of one or more cleaning and/or antimicrobial agents intended to be present in the liquid, a pH of the liquid, a temperature of the liquid, a turbidity of the liquid (e.g., which may include a soil level in the liquid), an oxidative reductive potential (ORP) of the liquid (e.g., conductivity probe measurements), and/or a total dissolved solids level of the liquid.

Liquid characteristic information determined based on information measured by sensor 36 may be stored in memory 54 of controller 50. In some examples, controller 50 may control tunnel washer 20 based on the measured property. Additionally or alternatively, controller 50 may transmit information concerning the measured characteristic/property to a remote computing device. For example, controller 50 may be implemented using one or more controllers, which may be located at the facility site containing washer 20. Controller 50 may communicate with one or more remote computing devices 56 via a network 58. For example, controller 50 may communicate with a geographically distributed cloud computing network, which may perform any or all of the functions attributed to controller 50 in this disclosure.

Network 58 can be configured to couple one computing device to another computing device to enable the devices to communicate together. Network 58 may be enabled to employ any form of computer readable media for communicating information from one electronic device to another. Also, network 58 may include a wireless interface, and/or a wired interface, such as the Internet, in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router may act as a link between LANs, enabling messages to be sent from one to another. Communication links within LANs may include twisted wire pair or coaxial cable, while communication links between networks may utilize analog telephone lines, full or fractional dedicated digital lines, Integrated Services Digital Networks (ISDNs), Digital Subscriber Lines (DSLs), wireless links including cellular and satellite links, or other communications links. Furthermore, remote computers and other related electronic devices may be remotely connected to either LANs or WANs via a modem and temporary telephone link.

In operation, liquid conveyance device 34 can generate a vacuum pressure to draw liquid into sensor housing 32 for analysis and subsequently generate a pressure to discharge the liquid in the sensor housing back out of the sensor housing. Accordingly, liquid conveyance device 34 may include a motive element, which may be a movable component within the device for generating a vacuum and/or positive pressures. For example, the motive element may move in one direction away from the sensor housing 32 to generate a vacuum drawing liquid from tunnel washer 20 into the sensor housing 32. The motive element may subsequently move in an opposite direction toward sensor housing 32 to generate a positive pressure pushing liquid in sensor housing 32 back out of the housing, e.g., and into tunnel washer 20. In different examples, liquid conveyance device 34 may be implemented using a positive displacement pump motive element, such as a piston or diaphragm.

Figure 2:
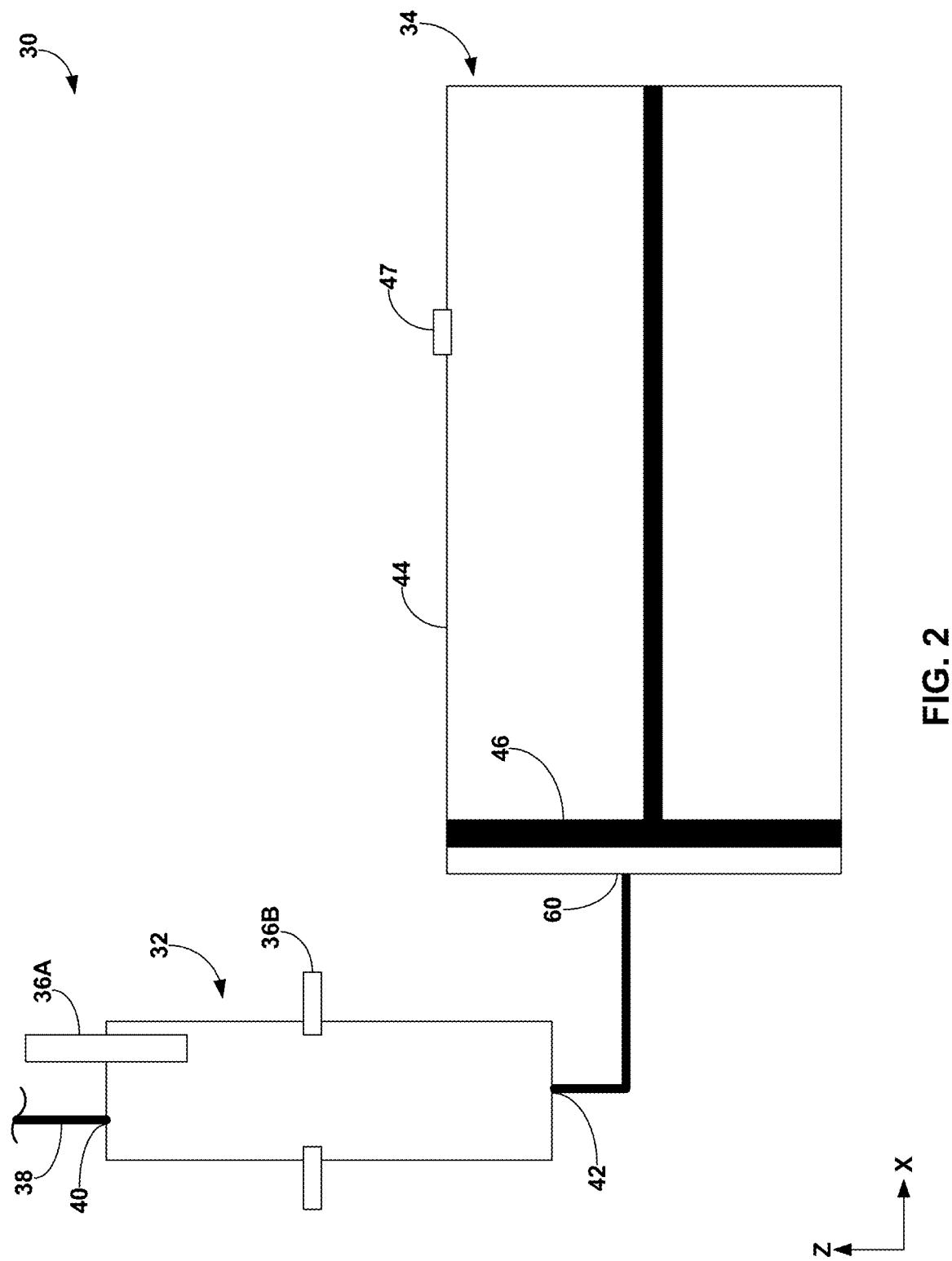
FIG. 2 is a sectional side view of an example configuration of a liquid sampling system illustrating an example configuration of a sensor housing and liquid conveyance device.

FIG. 2 is a sectional side view of an example configuration of liquid sampling system 30 illustrating an example configuration of sensor housing 32 and liquid conveyance device 34. In this example, sensor housing has a first opening 40 that can be connected to fluid line 38 to provide an inlet to the sensor housing from tunnel washer 20. Sensor housing 32 also includes a second opening 42, which is illustrated as being positioned on an opposite end of the sensor housing although may be located at any suitable position relative to first opening 40. Liquid conveyance device 34 is in fluid communication with second opening 42 of sensor housing 32. In some examples, a housing 44 of liquid conveyance device 34 is connected directly to sensor housing 32, e.g., to provide a housing-to-housing connection between second opening 42 of the sensor housing and an inlet opening of housing 44 without intervening conduit. In other examples, a fluid conduit is used to fluidly connect opening 42 of sensor housing 32 to a corresponding opening of housing 44 of liquid conveyance device 34. In either case, the liquid conveyance device 34 can be in pressure communication with sensor housing 32 to draw liquid into the sensor housing and expel liquid from the sensor housing.

In the illustrated configuration of FIG. 2, liquid conveyance device 34 is illustrated as having a piston 46 that is configured to translate back and forth within the pump housing 44. When piston 46 translates in a first direction (e.g., X-direction indicated on FIG. 2) such that the, piston is retracted in housing 44, the piston can generate a vacuum that draws liquid from tunnel washer 20 into sensor housing 32. The vacuum pressure may communicate with the tunnel washer via fluid line 38, first opening 40, and second opening 42 to which fluid conveyance device 34 is connected. After the fluid is analyzed within sensor housing 32, piston 46 can translate in a reverse direction (e.g., negative X-direction indicated on FIG. 2) to generate a positive pressure that expels the liquid out of the sensor housing via opening 40. The positive pressure generated by liquid conveyance device 34 may communicate with sensor housing 32 via the second opening 42 to which the fluid conveyance device is connected, forcing liquid in the sensor housing 32 back out via first opening 40. Liquid conveyance device 34 may include a vent 47 on an opposite side of piston 46 from the liquid side for venting air to and/or from housing 44 during actuation of the motive element.

Thus, in the illustrated arrangement, liquid extracted from tunnel washer 20 both enters and exits sensor housing 32 via the same opening 40. The liquid discharged from sensor housing 32 may be pushed back through fluid line 38 in a reverse direction from the direction in which the liquid was drawn into the sensor housing. In some applications, fluid line 38 is a single lumen line such that fluid pushed out of sensor housing 32 into fluid line 38 via opening 40 is pushed back to the processing chamber 26 from which the liquid was originally extracted. In other applications, fluid line 38 may have a branch or diversion to a drain or other discharge location, allowing liquid drawn into sensor housing 32 to be discharged from the housing without being reintroduced into the processing chamber 26 of tunnel washer 20. In still further examples, sensor housing 32 may have an additional opening separate from first opening 40 and second opening 42 that functions as a discharge outlet, e.g., connected to a discharge fluid line different than the fluid line 38. In these examples, fluid line 38 and opening 40 may function as inlets to draw liquid into sensor housing 32, while the separate opening in fluid line may function as outlets for discharging liquid from the sensor housing.

Although sensor housing can have a variety of different inlet and outlet opening configurations, configuring the sensor housing with a shared opening 40 through which liquid is both drawn into the sensor housing and discharge the sensor housing can be useful to prevent plugging and the accumulation of fouling material in the sensor housing. In operation, the material drawn into sensor housing 32 may contain solid particulates and other fouling material. By drawing liquid into sensor housing 32 and subsequently discharging the liquid from the same opening, a back-and-forth pulsating pressure may be applied. It has been found, in some applications, that this back-and-forth pulsating pressure and fluid movement has a tendency to purge solid material drawn into the sensor housing with a liquid sample for analysis, helping to prevent plugging of the liquid sampling system.

Liquid drawn into sensor housing 32 can be analyzed by one or more sensors 36, which is illustrated in FIG. 2 as a first sensor 36A and a second sensor 36B. First sensor 36A may be a sensor that includes a probe extending into sensor housing 32 and physically contacts liquid within the sensor housing, e.g., such as a temperature sensor, conductivity sensor, a pH sensor, and/or other direct contact sensor. Second sensor 36B, by contrast, may be a non-contact sensor that analyzes liquid within sensor housing 32 without physically contacting liquid. For example, second sensor 36B may be an optical sensor that includes an emitter and a detector to detect one or more optical characteristics of the liquid in sensor housing 32. It should be appreciated that the sensors illustrated in FIG. 2 are merely examples, and a liquid sampling system according to the disclosure may include a different number and/or different types of sensors without departing from the scope of disclosure.

In the example of FIG. 2, pump housing 44 of liquid conveyance device 34 is illustrated as being oriented horizontally with respect to gravity while sensor housing 32 is oriented vertically with respect to gravity. In other configurations, sensor housing 32 and/or pump housing 44 may have different orientations with respect to each other and/or with respect to gravity. For example, FIG. 3 is a sectional side view of another example configuration of liquid sampling system 30, where like reference numerals refer to like elements discussed above with respect to FIG. 2.

As shown in the example of FIG. 3, liquid sampling system 30 is also implemented using liquid conveyance device 34 that includes a piston 46 that translates within a pump housing 44. In this configuration, however, pump housing 44 is oriented vertically with respect to gravity (e.g., such that an opening 60 in the housing that communicates with second opening 42 of sensor housing 32 is positioned downward with respect to gravity). This alternative orientation of pump housing 44 has been found to be useful, in some applications, where the liquid drawn into sensor housing 32 and correspondingly pump housing 44 contains abrasive solid material. For example, when the liquid material being processed contains dirt, sand, or other grit, this particulate material may have a tendency to be drawn into pump housing 44 during the process of filling sensor housing 32. The particulate material may fall downwardly with respect to gravity while the liquid is retained in pump housing 44 (e.g., while a stationary volume of fluid in sensor housing 32 is undergoing analysis). When pump housing 44 is oriented horizontally, this particulate material may abrade piston 46 as it translates forward in piston housing 44, e.g., with the particulate material falling to the bottom of pump housing 44 wearing the bottom surface of the piston as it translates forward. Over time with repeated actuations of piston 46, this particulate material may have a tendency to degrade the piston to the point of failure, e.g., such that the piston 46 no longer seals with the inner wall surface of pump housing 44.

By orienting pump housing 44 vertically with respect to gravity in such applications (e.g., such that the inlet and/or outlet opening 60 of the pump housing is pointed downwardly with respect to gravity) particulate material drawn into the pump housing may fall to the outlet end 62 of the pump housing 44. As a result, the particulate material may not abrade piston 46 as it translates in pump housing 44. To help further protect piston 46, one or more stops 64 may be provided. The stops 64 may be spaced from outlet end 62 of pump housing 44 a distance, such as a distance of at least 1 mm, such as at least 10 mm, or at least 100 mm (e.g., a distance ranging from 10 mm to 2 cm).

Stop 64 may be a projection that the face of piston 46 contacts, preventing the piston from advancing fully to the outlet end 62 of pump housing 44. The space between stop 64 and outlet end 62 may provide a region that in which particulate material can collect in pump housing 44 without interfering with piston 46. During cycling of the piston, such collective material may be expected to be pushed out of the pump housing 44. Although stop 64 is illustrated in the orientation arrangement of FIG. 3, such a feature may be used in the orientation arrangement of FIG. 2 or yet other configurations as described herein. Further, although stop 64 is illustrated as being an internal stop that projects across a cross-section of pump housing 44, stop 64 may alternatively be implemented as an external feature that interacts with piston 46 and/or a drive mechanism of the piston.

FIG. 4 is a sectional side view of yet another example configuration of liquid sampling system 30, where like reference numerals refer to like elements discussed above with respect to FIGS. 2 and 3. In the example of FIG. 4, liquid sampling system 30 is shown being implemented using liquid conveyance device 34 that includes a membrane or diaphragm 48 that is configured to flex within the pump housing 44 to create a vacuum to draw liquid into sensor housing 32 and generate a pressure to push liquid out of the housing. Pump housing 44 with diaphragm 48 with can be oriented in any suitable way relative to sensor housing 32, including horizontally as discussed with respect to FIG. 2 or vertically with opening 60 pointing downwardly as discussed with respect to FIG. 3.

Diaphragm 48 may flex away from opening 60 (e.g., in the negative Z-direction indicated on FIG. 4) to create a vacuum, drawing liquid into sensor housing 32. Diaphragm 48 may further flex towards opening 60 (e.g., in the positive Z-direction indicated on FIG. 4) to create a pressure pulse, pushing the liquid in sensor housing 32 back out of the housing. Diaphragm 48 may be formed of a flexible material, such as a rubber, thermoplastic, or polytetrafluoroethylene material.

Configuring liquid conveyance device 34 with a diaphragm 48 instead of a piston 46 or element that translates along the length of the pump housing 44 may be useful when dealing with solid-containing liquids carrying abrasive particulates. Diaphragm 48 may be secured about its periphery to pump housing 44, e.g., such that the diaphragm flexes inside the housing but remains anchored and stationary about its perimeter. As a result, if abrasive particulate enters pump housing 44, the particulate is not allowed to interact in a space between the motive element (diaphragm 48) and the surface of the wall. This can be useful to maintain prolonged operation of liquid conveyance device 34 between any routine maintenance that may be typically provided.

Independent of the specific configuration of liquid conveyance device 34, pump housing 44 of the liquid conveyance device may be sized relative to sensor housing 32. To repeatedly measure the characteristics of different samples of fluid, liquid conveyance device 34 may substantially completely purge the sensor housing 32 of liquid and refill it with fresh liquid during cycling. Accordingly, liquid conveyance device 34 may be sized to draw a volume of liquid greater than the volume of sensor housing 32. The volume of sensor housing 32 may be considered the amount of liquid that can be held in the sensor housing went completely full.

By configuring liquid conveyance device 34 to draw a volume of liquid greater than the volume of sensor housing 32, the liquid conveyance device may pull at least as much liquid as is needed to fill the sensor housing. Further, as liquid conveyance device 34 may typically draw more than the volume of sensor housing 32, additional liquid may be drawn past sensor housing 32 and into the liquid conveyance device itself (e.g., via the second opening 42 and opening 60 of pump housing 44 in communication therewith). Additionally or alternatively, additional liquid drawn by liquid conveyance device 34 may account for any volume of liquid contained in fluid line 38 and/or any fluid line between sensor housing 32 and liquid conveyance device 34.

For example, the capacity of liquid conveyance device 34 may be effective to completely fill the fluid space between the source of liquid from which the sample is being extracted (e.g., processing chamber 26 of tunnel washer 20) and the liquid conveyance device 34. This capacity of liquid conveyance device 34 may further be effective to completely purge the fluid space between liquid conveyance device 34 and the discharge location following analysis liquid sample, which may be back to the original source. The amount of fluid space between the source and liquid conveyance device 34 may be the combined capacity of fluid line 38 and sensor housing 32. While liquid conveyance device 34 may typically operate to completely fill sensor housing 32 with liquid for analysis, in other examples, the liquid conveyance device may only partially fill the sensor housing, e.g., with an amount of liquid suitable for one or more sensors 36 to interact with the liquid.

The amount of liquid drawn and/or discharged by liquid conveyance device 34 may be controlled by controlling the size of pump housing 44 and the distance the motive element (e.g., piston 46, diaphragm 48) travels in the housing. In some examples, the motive element of liquid conveyance device is configured to draw a volume of liquid at least 1.5 times the volume of sensor housing 32, such as at least twice the volume of the sensor housing. For example, a ratio of the volume of liquid drawn by liquid conveyance device 34 divided by the volume of sensor housing 32 may range from 1.2 to 20, such as from 1.5 to 15, 2 to 10, or 2 to 5.

The specific size and dimensions of sensor housing 32 and pump housing 44 may vary depending on the desired application. In some examples, however, sensor housing 32 may have a volume ranging from 100 mL to 500 mL. In such an application, liquid conveyance device 34 may be designed to draw a volume of liquid ranging from 1 mm to 2.5 mL during operation. When sensor housing 32 is connected to a source by fluid line 38, the fluid line may have a volume or liquid capacity less than the volume of the sensor housing. Additionally or alternatively, when liquid conveyance device 34 is connected to sensor housing 32 by a fluid line, this fluid line may have a volume or liquid capacity less than the volume of the sensor housing. Otherwise, if one or more fluid lines in the system are long and/or have a larger capacity, the capacity of liquid conveyance device 34 may be adjusted to account for the long holding volume within the one or more lines.

Liquid conveyance device 34 may be powered by any suitable power source, such as electrical power or pneumatic power. In some configurations, a motive fluid such as pressurized air or hydraulic fluid is used to drive the motive element inside of pump housing 44 to translate back and forth. Independent of the type of power source used to drive liquid conveyance device 34, the liquid conveyance device may generate a vacuum pressure sufficient to draw liquid from the source to fill sensor housing 32 and subsequently generate a positive pressure sufficient to purge the liquid from the sensor housing. In some applications, liquid conveyance device 34 is configured to pressurize liquid drawn into the sensor housing 32 to a pressure greater than 25 psig, such as greater than 50 psig, or greater than 75 psig. Configuring liquid conveyance device 34 to generate a sufficiently high pressure for expelling liquid from sensor housing 32 can be useful to help purge solid materials, particulates, or other debris drawn into the sensor housing back out of the sensor housing.

With further reference to FIG. 1, controller 50 can control operation of liquid sampling system 30 to extract and analyze a liquid sample and subsequently discharge the liquid sample from the system. For example, controller 50 can control the motive element (e.g., piston 46, diaphragm 48) of the liquid conveyance device to draw liquid from processing chamber 26 of tunnel washer 20 into sensor housing 32. Controller 50 may control the motive element by controlling a power source (e.g., motive fluid) that drives movement of the motive element. Controller 50 may hold the liquid drawn into sensor housing 32 for a period of time sufficient for the one or more sensors to measure one or more properties of the liquid drawn into the sensor housing. Controller 50 may hold the liquid in sensor housing 32 by maintaining the motive element in a retracted position. The amount of time needed for a sensor to measure a corresponding property of the liquid may vary depending on the type of sensor from a fraction of a second (e.g., 1 second or less, such as 0.5 seconds or less, or 0.1 seconds or less) to more than a second (e.g., from 1 second to 1 minute, such as from 1 second to 10 seconds, or from 1 second to 5 seconds).

Upon controller 50 receiving a signal from sensor 36 indicating that the property of the liquid has been measured, the controller can control the motive element to discharge the liquid from sensor housing 32 back out of the housing. Again, controller 50 may control the motive element by controlling a power source that drives movement of the motive element.

With some types of sensors 36, it is desirable to keep the sensor fluid wet between uses to prevent a sensor element from drying out. Accordingly, when not in active sampling mode, controller 50 may control liquid sampling system 30 to keep sensor housing 32 liquid full rather than discharging the liquid from the housing after analysis. Controller 50 may subsequently purge the liquid from the sensor housing before performing a subsequent liquid sample extraction and analysis. Additionally or alternatively, liquid sampling system 30 may be implemented as a closed system that does not introduce air into sensor housing 32 between sample extractions (e.g., beside any air leakage that may normally occur because of manufacturing tolerances). When so configured, sensor(s) 36 may remain wetted even between samples even if sensor housing 32 is evacuated of liquid following analysis of a liquid sample.

A liquid sampling system according to the disclosure can be useful for extracting samples of liquid from a source where the samples contain solid materials, such as agglomerates, particulates, or other materials that will be drawn into a sensor chamber and have a tendency to cause plugging and/or fouling problems. The liquid sampling system may be implemented with a sensor housing positioned between a liquid source and a liquid conveyance device that provides alternating negative and positive pressure. The resulting back and forth liquid flow created by this arrangement can help release and remove the undesired solid materials that may be drawn into the sensor housing, helping to keep the sensor housing clean for repeated and subsequent samplings.

To avoid premature plugging, a liquid sampling system according to disclosure may be implemented as a filtration-free system that is devoid of any filtration elements (e.g., screen) that liquid flows through between the source and the sensor housing. By eliminating a filtration element, additional solid material that may otherwise be filtered out may be drawn into the sensor housing. However, this solid material drawn into the sensor housing may be purged back out of the housing when pressure is applied to discharge the liquid sensor housing during cycling. While a liquid sampling system according to disclosure may be implemented without a filtration element, it should be appreciated that a filtration element may optionally be used in the disclosure is not limited in this respect. For example, a filtration element with comparatively large pores may be located along fluid line 38 and/or at tunnel washer 20 to help prevent large particulate from entering the liquid sampling system.

The techniques described in this disclosure, including functions performed by a controller, control unit, or control system, may be implemented within one or more of a general purpose microprocessor, digital signal processor (DSP), application specific integrated circuit (ASIC), field programmable gate array (FPGA), programmable logic devices (PLDs), or other equivalent logic devices. Accordingly, the terms "processor" or "controller," as used herein, may refer to any one or more of the foregoing structures or any other structure suitable for implementation of the techniques described herein.

The various components illustrated herein may be realized by any suitable combination of hardware, software, and firmware. In the figures, various components are depicted as separate units or modules. However, all or several of the various components described with reference to these figures may be integrated into combined units or modules within common hardware, firmware, and/or software. Accordingly, the representation of features as components, units or modules is intended to highlight particular functional features for ease of illustration, and does not necessarily require realization of such features by separate hardware, firmware, or software components. In some cases, various units may be implemented as programmable processes performed by one or more processors or controllers.

Any features described herein as modules, devices, or components may be implemented together in an integrated logic device or separately as discrete but interoperable logic devices. In various aspects, such components may be formed at least in part as one or more integrated circuit devices, which may be referred to collectively as an integrated circuit device, such as an integrated circuit chip or chipset. Such circuitry may be provided in a single integrated circuit chip device or in multiple, interoperable integrated circuit chip devices.

If implemented in part by software, the techniques may be realized at least in part by a computer-readable data storage medium (e.g., a non-transitory computer-readable storage medium) comprising code with instructions that, when executed by one or more processors or controllers, performs one or more of the methods and functions described in this disclosure. The computer-readable storage medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), embedded dynamic random access memory (eDRAM), static random access memory (SRAM), flash memory, magnetic or optical data storage media. Any software that is utilized may be executed by one or more processors, such as one or more DSP's, general purpose microprocessors, ASIC's, FPGA's, or other equivalent integrated or discrete logic circuitry.

Various examples have been described. These and other examples are within the scope of the following claims.

The invention claimed is:

1. A liquid sampling system for a textile washer comprising:
   a textile washer having a processing chamber;
   a liquid sampling system having a fluid line in fluid communication with the processing chamber of the textile washer, the liquid sampling system including:
      a sensor housing having a first opening connected to the fluid line and a second opening;
      at least one sensor positioned to measure a property of a liquid drawn into the sensor housing; and
      a liquid conveyance device having an opening in fluid communication with the second opening of the sensor housing and a motive element,
         the motive element being configured to draw a volume of liquid into the liquid conveyance device through the opening, thereby drawing liquid from the processing chamber of the textile washer via the fluid line and into the sensor housing, and
         the motive element being configured to subsequently discharge the volume of liquid from the liquid conveyance device back out through the opening, thereby pushing the liquid in the sensor housing out of the sensor housing.

2. The system of claim 1, wherein the motive element is configured to push the liquid in the sensor housing out of the first opening connected to the fluid line and back into the processing chamber of the textile washer.

3. The system of claim 1, wherein the sensor housing defines a sensor housing volume, and the volume of liquid the motive element is configured to draw is greater than the volume of the sensor housing.

4. The system of claim 3, wherein a ratio of the volume of liquid the motive element is configured to draw into the liquid conveyance device divided by the volume of the sensor housing ranges from 2 to 10.

5. The system of claim 1, wherein:
   the textile washer having the processing chamber is a tunnel washer having an inlet, an outlet, and a plurality of processing chambers between the inlet and the outlet, and
   the plurality of processing chambers include a wash chamber, an oxidizing chamber, and a rinse chamber,
   the fluid line of the liquid sampling system is in fluid communication with the wash chamber or the oxidizing chamber.

6. The system of claim 1, wherein the liquid conveyance device comprises a pump housing and the motive element comprises a piston positioned to translate within the pump housing, the piston generating a vacuum when retracted within the pump housing to draw the volume of liquid into the pump housing and the piston pressurizing the volume of liquid drawn within the pump housing when advanced in an opposite direction within the pump housing to discharge the volume of liquid back out of the pump housing.

7. The system of claim 6, wherein the pump housing is oriented vertically with respect to gravity and includes a piston stop spaced from an outlet end of the pump housing, the piston stop being configured to stop the piston from advancing fully to the outlet end of the pump housing and thereby provide a debris collection space.

8. The system of claim 1, wherein the liquid conveyance device comprises a pump housing and the motive element comprises a membrane configured to flex within the pump housing, the membrane generating a vacuum when flexed into the pump housing to draw the volume of liquid into the pump housing and the membrane pressurizing the volume of liquid drawn within the pump housing when flexed in an opposite direction within the pump housing to discharge the volume of liquid back out of the pump housing.

9. The system of claim 1, wherein the liquid conveyance device is configured to pressurize the volume of liquid to a pressure greater than 50 psig when discharging the volume of liquid from the liquid conveyance device.

10. The system of claim 1, wherein the at least one sensor includes a sensor selected from the group consisting of a temperature sensor, a pH sensor, a conductivity sensor, an optical sensor, an oxidation reduction potential sensor, a total dissolved solids sensor, and combinations thereof.

11. The system of claim 1, further comprising a controller communicatively coupled to the at least one sensor and the liquid conveyance device, wherein the controller is configured to:
   control the motive element of the liquid conveyance device to draw liquid from the processing chamber of the textile washer into the sensor housing and hold the liquid drawn into the sensor housing for a period of time sufficient for the at least one sensor to measure the property of the liquid drawn into the sensor housing;
   receive a signal from the at least one sensor indicative of the property measured by the sensor; and
   control the motive element of the liquid conveyance device to discharge the liquid drawn into the sensor housing out of the sensor housing.

12. The system of claim 11, wherein the controller is configured to repeat a process of controlling the motive element of the liquid conveyance device to draw liquid into the sensor housing, receiving the signal from the at least one sensor, and controlling the motive element of the liquid conveyance device to discharge the liquid drawn into the sensor housing out of the sensor housing at least once every 10 seconds during operation.

13. The system of claim 11, wherein the controller is configured to at least one of transmit the property measured by the sensor to a remote computing device and control the textile washer based on the property measured by the sensor.

14. The system of claim 1, further comprising a fluid line connecting the second opening of the sensor housing to the opening of the liquid conveyance device, the fluid line having a volume less than the volume of the sensor housing.

15. A method comprising:
drawing a sample of liquid out of a processing chamber of a textile washer by driving a motive element of a liquid conveyance device in fluid communication with the processing chamber and having a sensor housing positioned between the motive element and the processing chamber, thereby filling the sensor housing with liquid from the processing chamber;
measuring a property of the liquid drawn into the sensor housing using at least one sensor; and
pushing the liquid drawn into the sensor housing back out of the sensor housing and back into the processing chamber of the textile washer by driving the motive element of the liquid conveyance device.

16. The method of claim 15, wherein drawing the sample of liquid out of the processing chamber comprises drawing a volume of liquid greater than a volume of the sensor housing out of the processing chamber.

17. The method of claim 15, wherein the textile washer is a tunnel washer having a plurality of processing chambers including a pre-wash chamber, a wash chamber, and a rinse chamber, and drawing the sample of liquid out of the processing chamber comprises drawing the sample of liquid out of the wash chamber.

18. The method of claim 15, wherein the sample of liquid comprises from 0.05 to 5 weight percent solids.

19. The method of claim 15, wherein the liquid conveyance device comprises a pump housing and the motive element comprises a piston that translates within the pump housing, the piston generating a vacuum when retracted within the pump housing to draw the sample of liquid and the piston pressurizing liquid drawn into the pump housing when advanced in an opposite direction to push the liquid drawn into the sensor housing back out of the sensor housing.

20. The method of claim 15, wherein the liquid conveyance device comprises a pump housing and the motive element comprises a membrane configured to flex within the pump housing, the membrane generating a vacuum when flexed into the pump housing to draw the sample of liquid and the membrane pressurizing the liquid drawn into the pump housing when flexed in an opposite direction within the pump housing to push the liquid drawn into the sensor housing back out of the sensor housing.

21. The method of claim 15, wherein pushing the liquid drawn into the sensor housing back out of the sensor housing and back into the processing chamber of the textile washer comprises pushing the liquid drawn into the sensor housing back out of the sensor housing at a pressure of greater than 50 psig.

22. The method of claim 15, wherein the at least one sensor includes a sensor selected from the group consisting of a temperature sensor, a pH sensor, a conductivity sensor, an optical sensor, an oxidation reduction potential sensor, a total dissolved solids sensor, and combinations thereof.

23. A liquid sampling system comprising:
a sensor housing that has a first opening and a second opening and that defines a volume within the sensor housing;
at least one sensor positioned to measure a property of a liquid drawn into the sensor housing; and
a liquid conveyance device having an opening in fluid communication with the second opening of the sensor housing and a motive element, the motive element being configured to draw a volume of the liquid greater than the volume of the sensor housing into the liquid conveyance device via the opening, thereby drawing liquid into the sensor housing, and subsequently discharge the volume of liquid drawn into the liquid conveyance device back out through the opening.

24. The system of claim 23, wherein the motive element is configured to draw the volume of liquid into the liquid conveyance device through the first and second openings and the volume of the sensor housing and subsequently discharge the volume of liquid through the first and second openings and the volume of the sensor housing, thereby flushing the sensor housing through filling and discharging of the liquid conveyance device.

25. The system of claim 23, wherein a ratio of the volume of liquid the motive element is configured to draw into the liquid conveyance device divided by the volume of the sensor housing ranges from 2 to 10.

* * * * *